(12) United States Patent
Miyagi et al.

(10) Patent No.: US 7,795,233 B2
(45) Date of Patent: Sep. 14, 2010

(54) COMPOSITION COMPRISING DOUBLE STRANDED RNA THAT INHIBITS EXPRESSION OF NEU3 AND METHOD FOR TREATING CANCER

(75) Inventors: Taeko Miyagi, Sendai (JP); Tadashi Wada, Watari-cho (JP); Kazunori Yamaguchi, Sendai (JP)

(73) Assignee: Miyagi Ken, Sendai-shi, Miyagi (JP)

( * ) Notice: Subject to any disclaimer, the term of this patent is extended or adjusted under 35 U.S.C. 154(b) by 447 days.

(21) Appl. No.: 11/719,517

(22) PCT Filed: Nov. 15, 2005

(86) PCT No.: PCT/JP2005/020955

§ 371 (c)(1),
(2), (4) Date: May 16, 2007

(87) PCT Pub. No.: WO2006/054555

PCT Pub. Date: May 26, 2006

(65) Prior Publication Data

US 2009/0149402 A1 Jun. 11, 2009

(30) Foreign Application Priority Data

Nov. 19, 2004 (JP) ............................. 2004-335774

(51) Int. Cl.
*A01N 43/04* (2006.01)
*C07H 21/04* (2006.01)

(52) U.S. Cl. ...................................... 514/44; 536/24.5

(58) Field of Classification Search ................. 514/44; 536/24.5
See application file for complete search history.

(56) References Cited

U.S. PATENT DOCUMENTS

| 6,225,454 | B1 | 5/2001 | Miyagi et al. |
| 6,506,559 | B1 * | 1/2003 | Fire et al. ........................ 435/6 |
| 6,573,099 | B2 * | 6/2003 | Graham ....................... 435/455 |

FOREIGN PATENT DOCUMENTS

| EP | 0 984 061 | 3/2000 |
| JP | 2003-55399 A | 2/2003 |

OTHER PUBLICATIONS

Miyagi, et al. "Aberrant Expression of Sialidase in Cancer," *Trends in Glycoscience and Glycotechnology*, vol. 16, No. 92, pp. 371-381, Nov. 2, 2004.
Miyagi, et al. "A Crucial Role of Plasma Membrane-Associated Sialidase (NEU3) in the Survival of Human Cancer Cells," *Glycobiology*, vol. 14, No. 11, p. 1176, Oct. 21, 2004.
Duxbury, et al. RNA Interference: A Practical Approach, *J. Surg. Res.*, vol. 117, No. 2, pp. 339-344, 2004.
Sasaki, et al. "Overexpression of Plasma Membrane-Associated Sialidase Attenuates Insulin Signaling in Transgenic Mice," *J. Biol. Chem*, vol. 278, No. 30, pp. 27896-27902, 2003.
Kakugawa, et al. "Up-Regulation of Plasma Membrane-Associated Ganglioside Sialidase (Neu3) in Human Colon Cancer and Its Involvement in Apoptosis Suppression," *Proc. Natl. Acad. Sci. USA*, vol. 99, No. 16, pp. 10718-10723, 2002.
Miyagi, et al. "XVIII International Symposium on Glycoconjugates," L028, [Online], Sep. 4, 2005, Firenze, Italy, Abstract.

* cited by examiner

*Primary Examiner*—J. E Angell
(74) *Attorney, Agent, or Firm*—Knobbe, Martens, Olson & Bear, LLP

(57) ABSTRACT

A pharmaceutical composition for treating cancer or diabetes which contains the following double-stranded RNA (A) or (B):
(A) a double-stranded RNA having a sequence represented by SEQ ID NO:2, SEQ ID NO:4 or SEQ ID NO:8.
(B) a double-stranded RNA which has a sequence of 20 to 30 nucleotides that is identical to a partial sequence of a gene encoding human plasma membrane-associated sialidase (NEU3) and contains the sequence represented by SEQ ID NO: 2, SEQ ID NO: 4, or SEQ ID NO: 8, and the double-stranded RNA inhibits the expression of a gene encoding human plasma membrane-associated sialidase (NEU3).

9 Claims, 2 Drawing Sheets

[Fig. 1]
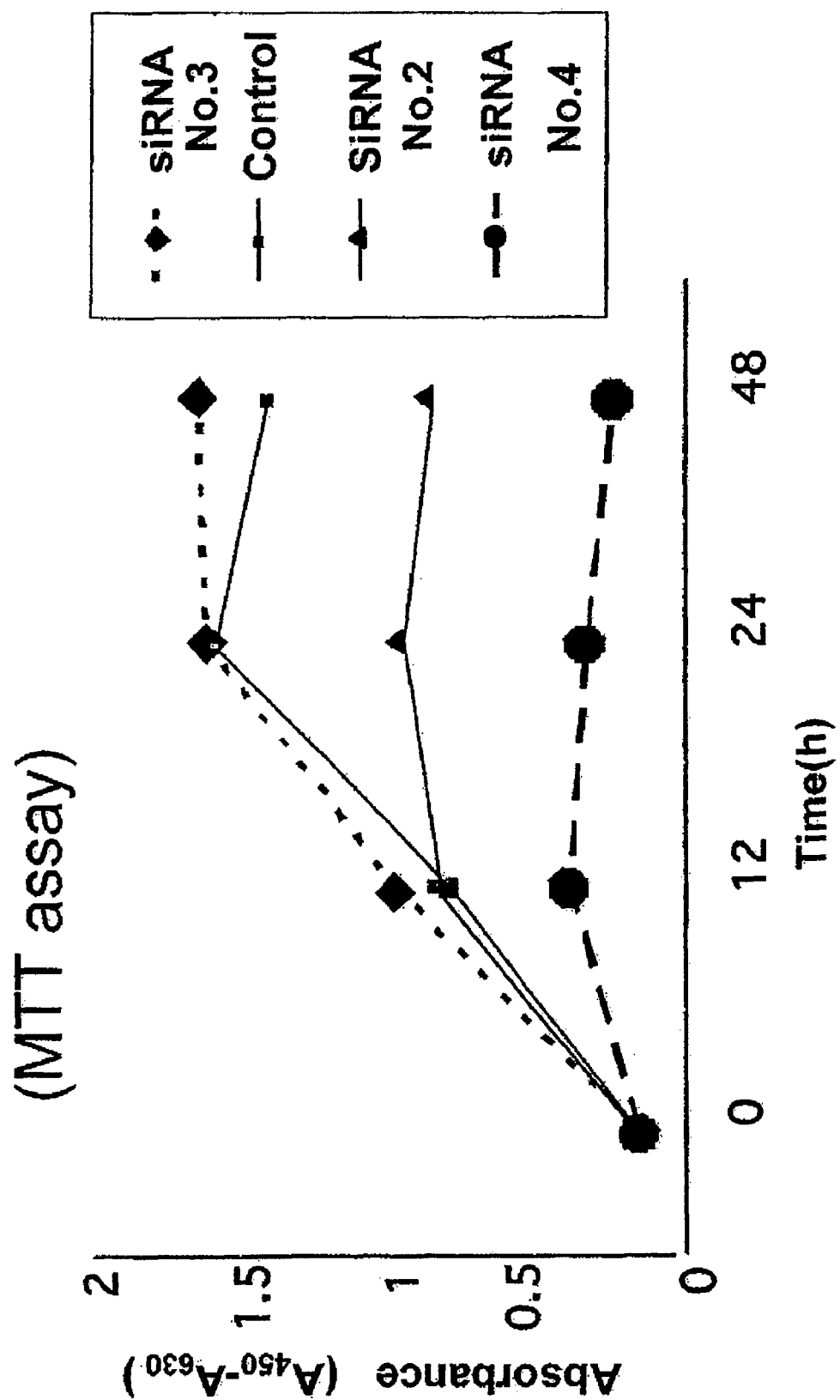

[Fig. 2]
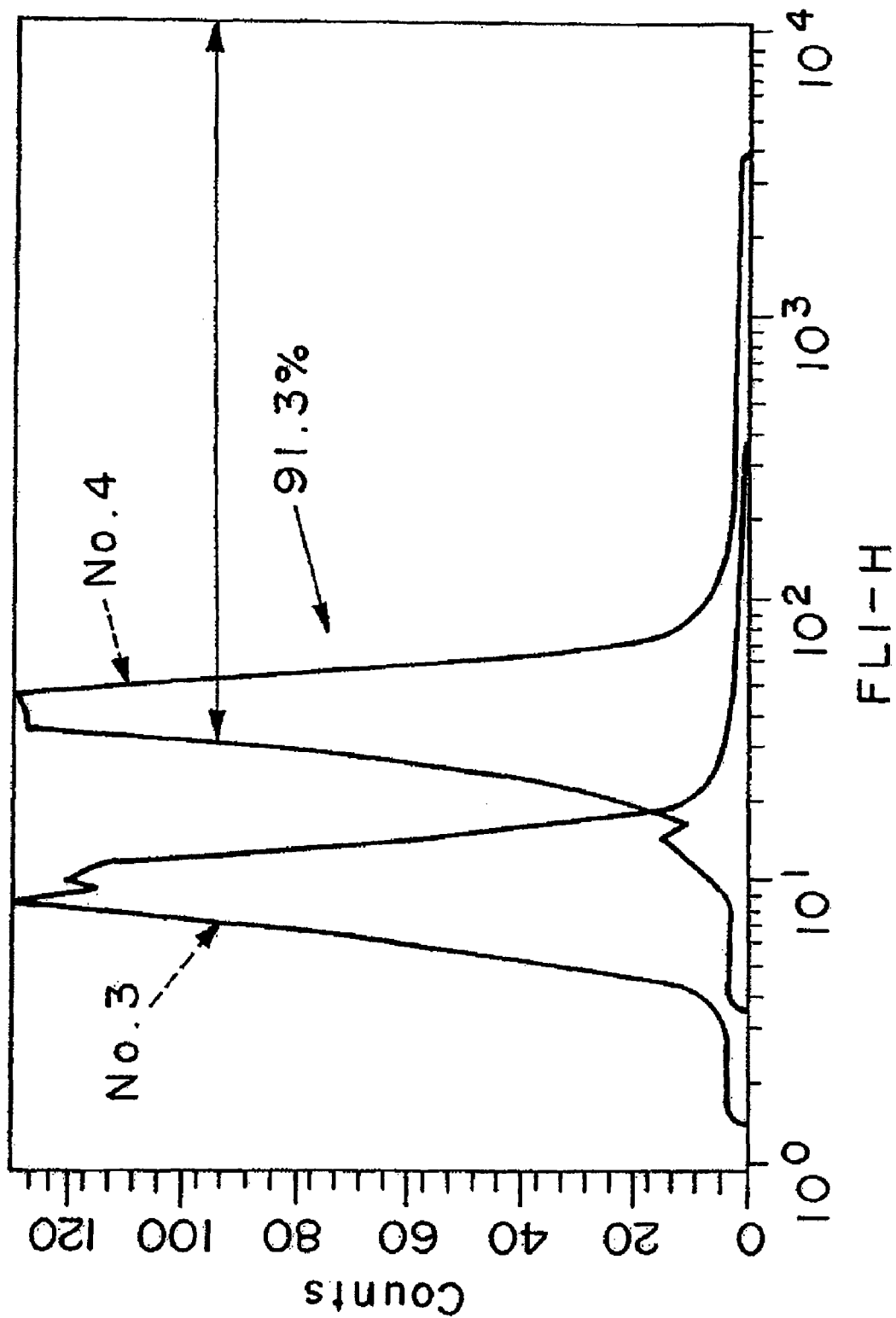

COMPOSITION COMPRISING DOUBLE STRANDED RNA THAT INHIBITS EXPRESSION OF NEU3 AND METHOD FOR TREATING CANCER

RELATED APPLICATIONS

This is the U.S. National Phase under 35 U.S.C. §371 of International Application PCT/JP2005/020955, filed Nov. 15, 2005, which was published in a language other than English, which claims priority of JP 2004-335774, filed Nov. 19, 2004.

TECHNICAL FIELD

The present invention relates to a pharmaceutical composition for treating cancer or diabetes.

BACKGROUND ART

The inventors of the present application have successfully isolated a human plasma membrane-associated sialidase (NEU3) gene (see, Patent Document 1). Meanwhile, they have discovered that the expression of the gene is enhanced in various human cancers including human colon cancer (see, Non-Patent Document 1), prostate cancer, head and neck cancer and etc. with few exceptions. On the other hand, a transgenic mouse into which the gene was introduced were found to develop diabetes (see, Non-patent Document 2), and the polymorphism in the NEU3 gene in patients with diabetes was discovered and found to be deeply involved in onset of Type 2 diabetes.

As described above, it has been suggested that the enhancement of the expression level of the human plasma membrane-associated sialidase is deeply involved in canceration of cells and onset of diabetes. Based on this finding, the inventors of the present invention have provided a method of diagnosing cancer using an antibody that specifically recognizes a human plasma membrane-associated sialidase (see, Patent Document 2).

On the other hand, in recent years, as a method for specifically inhibiting the expression of a particular gene, a method using RNA interference (RNAi) caused by a double-stranded RNA having a sequence complementary to the gene has attracted attention. The mechanism of the method is considered as follows.

When a double-stranded RNA having a sequence complementary to a gene targeted for expression inhibition is incorporated into cells, the double-stranded RNA is cleaved with Dicer enzyme which belongs to the RNAase III family and processed into short double-stranded RNA fragments of about 21 to 23 nucleotides. The antisense strands of the RNA fragments are separately bound to proteins having ribonuclease activities to form complexes referred to as RISC(RNA-induced silencing complex). It is considered that when an antisense strand in RISC is bound to mRNA of a target gene, the mRNA is cleaved to inhibit the expression of the target gene (see, Non-patent Document 3).

It is generally known that, when a long-chain (of at least hundreds of nucleotides) double-stranded RNA is used for inhibiting the expression of a gene of a nematode, a fungus, Drosophila, a plant, or the like, a higher effect of inhibiting the expression can be achieved. However, in a mammal cell system, introduction of a long-chain double-stranded RNA activates an interferon signal pathway to cause cytotoxicity, thus it is considered that the method is difficult to be applied to mammal cells.

However, thereafter, a method of avoiding interferon responses by introducing a short double-stranded RNA (for example, of about 21 to 23 nucleotides) in advance has been developed, and became applicable to mammal cells (see, Non-Patent Document 4). Such a short double-stranded RNA is referred to as siRNA (small interfering RNA) and expected to be applied to a gene function analysis or a gene therapy using viruses (for example, see Non-Patent Document 5).

However, a siRNA that inhibits the expression of a human plasma membrane-associated sialidase (NEU3) gene has not been known, and a pharmaceutical composition for treating cancer or diabetes by using such a siRNA has not been known.

Patent Document 1: JP 3088681 B

Patent Document 2: JP 2003-55399 A

Non Patent Document 1: Proc. Natl. Acad. Sci., 99, 10718-10723, 2002

Non Patent Document 2: J. Biol. Chem., 278, 27896-27902, 2003

Non Patent Document 3: Molecular Medicine, 41(1), 10-29, 2004

Non Patent Document 4: Nature, 411, 494-498, 2001

Non Patent Document 5: Virus, 53(1), p 7-14, 2003

DISCLOSURE OF THE INVENTION

The present invention have been made from the above-described viewpoint, and an object of the present invention is to provide a pharmaceutical composition for treating cancer or diabetes which contains a siRNA efficiently inhibiting the expression of a human plasma membrane-associated sialidase (NEU3) gene.

The inventors of the present invention have made extensive studies for achieving the above-described object, and as a result, they have discovered that a siRNA having a particular sequence efficiently inhibits the expression of a human plasma membrane-associated sialidase (NEU3) gene, thereby completing the present invention.

That is, the summary of the present invention is as follows.

(1) A pharmaceutical composition for treating cancer or diabetes comprising a double-stranded RNA shown in (A) or (B):

(A) a double-stranded RNA having a sequence represented by SEQ ID NO: 2, SEQ ID NO: 4, or SEQ ID NO: 8;

(B) a double-stranded RNA which has a sequence of 20 to 30 nucleotides that is identical to a partial sequence of a gene encoding human plasma membrane-associated sialidase (NEU3) and contains the sequence represented by SEQ ID NO: 2, SEQ ID NO: 4, or SEQ ID NO: 8, and the double-stranded RNA inhibits the expression of a gene encoding human plasma membrane-associated sialidase (NEU3).

(2) The pharmaceutical composition according to (1), wherein the double-stranded RNA has 20 to 27 nucleotides.

(3) The pharmaceutical composition according to (1), wherein the double-stranded RNA further comprises 3'-protruding end of 1 to 4 nucleotides.

(4) The pharmaceutical composition for treating cancer or diabetes comprising a vector having a nucleotide sequence capable of expressing the double-stranded RNA according to any one of (1) to (3) in human cells.

(5) The pharmaceutical composition according to any one of (1) to (4), wherein the cancer or diabetes causes an increase in the expression of a human plasma membrane-associated sialidase (NEU3) gene.

DESCRIPTION OF THE PREFERRED EMBODIMENTS

Hereinafter, preferred embodiments of the present invention will be described in detail. However, the present invention is not limited to the following preferred embodiments and can be modified freely within the scope of the present invention. Note that, in the present description, percentage indicates by mass unless otherwise specified.

A pharmaceutical composition for treating cancer or diabetes of the present invention (hereinafter, sometimes merely referred to as "the pharmaceutical composition of the present invention") comprises the following double-stranded RNA (A) or (B):

(A) a double-stranded RNA having a sequence represented by SEQ ID NO: 2, SEQ ID NO: 4, or SEQ ID NO: 8.

(B) a double-stranded RNA which has a sequence of 20 to 30 nucleotides that is identical to a partial sequence of a gene encoding human plasma membrane-associated sialidase (NEU3) and contains the sequence represented by SEQ ID NO: 2, SEQ ID NO: 4, or SEQ ID NO: 8, and the double-stranded RNA inhibits the expression of a gene encoding human plasma membrane-associated sialidase (NEU3).

The double-stranded RNA to be used in the present invention is a siRNA as described above and inhibits the expression of a gene encoding human plasma membrane-associated sialidase (NEU3). The sequence of the gene is known and disclosed as GenBank/DDBJ accession No. AB008185 (JP 3088681 B).

The double-stranded RNA to be used in the present invention includes: (A) a double-stranded RNA having a sequence represented by SEQ ID NO: 2, SEQ ID NO: 4, or SEQ ID NO: 8; or (B) a double-stranded RNA which has a sequence of 20 to 30 nucleotides that is identical to a partial sequence of a gene encoding human plasma membrane-associated sialidase (NEU3) and contains the sequence represented by SEQ ID NO: 2, SEQ ID NO: 4, or SEQ ID NO: 8, and the double-stranded RNA inhibits the expression of a gene encoding human plasma membrane-associated sialidase (NEU3).

Herein, the "double-stranded RNA which has a sequence identical to" a partial sequence of a gene means a double strand comprising an RNA or DNA having a sequence identical to a partial sequence of the gene (antisense strand) and a RNA having a sequence complementary thereto (sense strand). Note that an RNA having a sequence "identical to" a sequence of a DNA means an RNA having the same nucleotide sequence as the DNA except that thymine has been replaced by uracil, while a DNA having a sequence "identical to" a sequence of an RNA means a DNA having the same nucleotide sequence as the RNA except that uracil has been replaced by thymine.

Meanwhile, the "a double-stranded RNA which has a sequence of 20 to 30 nucleotides that is identical to a partial sequence of a gene encoding human plasma membrane-associated sialidase (NEU3) and contains the sequence represented by SEQ ID NO: 2, SEQ ID NO: 4, or SEQ ID NO: 8" means: a double strand comprising an RNA or DNA that is identical to an antisense strand of a gene encoding NEU3 and has a sequence of 20 to 30 nucleotides comprising SEQ ID NO: 2 or a sequence identical thereto (antisense strand) and an RNA having a sequence complementary thereto (sense strand); a double strand comprising an RNA or DNA that is identical to an antisense strand of a gene encoding NEU3 and has a sequence of 20 to 30 nucleotides comprising SEQ ID NO: 4 or a sequence identical thereto (antisense strand) and an RNA having a sequence complementary thereto (sense strand); a double strand comprising an RNA or DNA that is identical to an antisense strand of a gene encoding NEU3 and has a sequence of 20 to 30 nucleotides comprising SEQ ID NO: 8 or a sequence identical thereto (antisense strand) and an RNA having a sequence complementary thereto (sense strand). Meanwhile, the "double-stranded RNA having the sequence represented by SEQ ID NO: 2, SEQ ID NO: 4, or SEQ ID NO: 8" means: a double strand comprising an RNA or DNA that comprises a sequence of 19 nucleotides represented by SEQ ID NO: 2 or a sequence identical thereto (antisense strand) and an RNA complementary thereto (sense strand); a double strand comprising an RNA or DNA that comprises a sequence of 19 nucleotides represented by SEQ ID NO: 4 or a sequence identical thereto (antisense strand) and an RNA complementary thereto (sense strand); or a double strand comprising an RNA or DNA that comprises a sequence of 25 nucleotides represented by SEQ ID NO: 8 or a sequence identical thereto (antisense strand) and an RNA complementary thereto (sense strand).

SEQ ID NO: 2 represents an RNA sequence identical to a DNA including nucleotides 704-722 of GenBank/DDBJ accession No. AB008185; SEQ ID NO: 4 represents an RNA sequence identical to a DNA including nucleotides 1009-1027 of GenBank/DDBJ accession No. AB008185; and SEQ ID NO: 8 represents an RNA sequence identical to a DNA including nucleotides 833-857 of GenBank/DDBJ accession No. AB008185.

The term "complementary" or "identical" does not always mean a completely complementary or identical sequence and may include a sequence with one, two, or three-nucleotides mismatches as long as mRNA of a target gene can be cleaved with a RISC complex into which a double-stranded RNA has been incorporated.

The sequence of the sense strand in a double-stranded RNA may be an RNA or DNA, but is preferably a RNA. Inhibition of the expression of a gene by an RNA-DNA hybrid is described in JP 2003-219893 A. In the present description, the sequence of a double-stranded RNA is represented as an RNA or DNA sequence of the antisense strand.

Meanwhile, the phrase "inhibiting the expression of a gene encoding human plasma membrane-associated sialidase (NEU3)" as used herein means that when a double-stranded RNA of the present invention is introduced into human cells, a RISC complex into which the antisense strain of the double-stranded RNA has been incorporated are formed and the RISC complex cleaves mRNA of a gene encoding human plasma membrane-associated sialidase (NEU3). Whether the expression of the gene encoding human plasma membrane-associated sialidase (NEU3) are inhibited can be confirmed by, for example: preparing cells into which a double-stranded RNA of the present invention is introduced and cells into which the RNA is not introduced under the same condition except for the introduction of the double-stranded DNA of the present invention; measuring the mRNA level of the full length of the gene, the protein level of human plasma membrane-associated sialidase (NEU3), which is a product of the gene, the value of sialidase activity and etc., in both the cells; and confirming that the mRNA level, protein level, or sialidase activity are reduced in the cells into which the double-stranded RNA of the present invention is introduced compared with those in the cells into which the double-stranded RNA of the present invention is not introduced. The mRNA level can be measured by a known method such as the Northern blot method or RT-PCR method as described in Examples below. Meanwhile, the protein level can be measured by a known method such as the RIA method or ELISA method. In addition, the sialidase activity can be measured by carrying out a test using ganglioside as a substrate as described in Examples below.

The double-stranded RNA to be used in the present invention is preferably a double-stranded RNA having the sequence represented by SEQ ID NO: 2, SEQ ID NO: 4, or SEQ ID NO: 8. However, a double-stranded RNA which has a sequence of 20 to 30 nucleotides that is identical to a partial sequence of a gene encoding human plasma membrane-associated sialidase (NEU3) and contains the sequence represented by SEQ ID NO: 2, SEQ ID NO: 4, or SEQ ID NO: 8, wherein the double-stranded RNA inhibits the expression of a gene encoding human plasma membrane-associated sialidase (NEU3), may be used as long as it has an effect of inhibiting the expression of a gene encoding human plasma membrane-associated sialidase (NEU3) as is the case with the above-described double-stranded RNA. In Examples below, it has been confirmed that a double-stranded RNA having a sequence represented by SEQ ID NO: 2, SEQ ID NO: 4, or SEQ ID NO: 8 has an effect of inhibiting the expression of a gene encoding human plasma membrane-associated sialidase (NEU3), but a double-stranded RNA which has a sequence of 20 to 30 nucleotides that is identical to a partial sequence of a gene encoding human plasma membrane-associated sialidase (NEU3) and contains the sequence represented by SEQ ID NO: 2, SEQ ID NO: 4, or SEQ ID NO: 8, wherein the double-stranded RNA inhibits the expression of a gene encoding human plasma membrane-associated sialidase (NEU3), can be used as long as it has an effect of inhibiting the expression of a gene encoding human plasma membrane-associated sialidase (NEU3) as is the case with the above-described double-stranded RNA. It has been reported that double-stranded RNAs of at most about 27 nucleotides have almost the same activities in some cases (see, J. Biol. Chem., 278, 15991-15997, 2003), and also in Examples below, it is confirmed that a double-stranded RNA having a sequence of 25 nucleotides is effective. Therefore, it is considered that the double-stranded RNA of about 20 to 30 nucleotides and contains the sequence represented by SEQ ID NO: 2, SEQ ID NO: 4, or SEQ ID NO: 8 has the same effect.

A double-stranded RNA to be used in the present invention has 19 to 30 nucleotides, and has preferably 19 to 27 nucleotides, more preferably 19 to 25 nucleotides, further preferably 19 to 23 nucleotides, most preferably 19 to 21 nucleotides. The numbers of the nucleotides as described herein refers to the numbers of nucleotides on the double-strand portion, and does not include the numbers of nucleotides on 3'-protruding ends as described below.

Meanwhile, in a double-stranded RNA to be used in the present invention, the sequences of the sense strand and anti-sense strand may have the same length, but either or both of the sequences may further have a 3'-protruding end (overhung) of 1 to 4 nucleotides. This is because the double-stranded RNA of the present invention becomes more stable in case that the RNA further has such a 3'-protruding end. Meanwhile, such a 3'-protruding end of 4 nucleotides or less is known to have no influence on the effect of inhibiting the expression of a target gene (see, Nat. Biotechnol., 20, 497-500, 2002).

The double-stranded RNA to be used in the present invention can be prepared by, for example: preparing a double-stranded RNA having a sequence identical to a gene encoding human plasma membrane-associated sialidase (NEU3) or a part thereof; and cleaving the RNA with Dicer enzyme. Dicer enzyme, which is commercially available, can be used. The double-stranded RNA may be prepared by an RNA polymerase reaction using, as a template, a double-stranded DNA which has a sequence of 20 to 30 nucleotides that is identical to a partial sequence of a gene encoding human plasma membrane-associated sialidase (NEU3) and contains the sequence represented by SEQ ID NO: 2, SEQ ID NO: 4, or SEQ ID NO: 8; or an RNA polymerase reaction using, as a template, a double-stranded DNA identical to the sequence represented by SEQ ID NO: 2, SEQ ID NO: 4, or SEQ ID NO: 8. Such double-stranded DNAs can be prepared by amplification using primers design based on the sequence of the gene.

When the double-stranded RNA obtained as above is cleaved with Dicer enzyme, a double-stranded RNA (siRNA) to be used in the present invention can be obtained. The siRNA thus obtained is a mixture of plural kinds of RNA molecules including a siRNA to be used in the present invention. The double-stranded RNA to be used in the present invention (siRNA) may be such a mixture or uniform RNA molecules obtained by purifying the mixture.

The double-stranded RNA to be used in the present invention (siRNA) may also be produced by chemical synthesis. That is, the double-stranded RNA to be used in the present invention (siRNA) can be obtained by: synthesizing a sense strand corresponding to a target sequence and an antisense strand; and annealing the strands. Moreover, the double-stranded RNA to be used in the present invention (siRNA) may be obtained by: inserting a synthetic DNA designed based on the sequence of a target gene into a commercially-available siRNA expression vector; and expressing it in an appropriate host.

Meanwhile, a pharmaceutical composition of the present invention may include a double-stranded RNA that is converted into a double-stranded RNA (siRNA) of interest by endogenous Dicer enzyme in a target cell.

Further, in another embodiment of the pharmaceutical composition of the present invention, the pharmaceutical composition of the present invention may comprise a vector having a nucleotide sequence which allows the double-stranded RNA to be expressed in target human cells, instead of the double-stranded RNA itself. Examples of the vector include a tandem siRNA expression vector and hairpin siRNA expression vector. Such vectors are not particularly limited and may be commercially available as long as they are capable of expressing a gene in human cells.

In the case of the tandem siRNA expression vector, the sense and antisense strands of a siRNA of interest are separately transcribed by an RNA polymerase in a cell, and then both strands are annealed to generate a siRNA of interest. On the other hand, in the case of the hairpin siRNA expression vector, an RNA including the sense and antisense strands of a siRNA of interest is transcribed by a RNA polymerase in a cell as a unit, and then both strands are bent in a region between the sense and antisense strands and are annealed to form a hairpin precursor RNA (shRNA; short hairpin RNA), followed by removal of a region of an unannealed single strand with RNAase in a cell to generate a siRNA of interest in a cell. Specific methods thereof are described in, for example, JP 2004-261002 A, "RNAi Experiment Protocol, revised edition, published by Yodosya Co., Ltd., published on Oct. 1, 2004", or the like. In the present specification, the "double-stranded RNA to be used in the present invention" may include a double-stranded RNA (siRNA) produced by an RNA that is expressed from the above-described vector in a human cell into which a vector having a nucleotide sequence, which allows the above-described double-stranded RNA of the present invention to be expressed in a human cell, is introduced.

The double-stranded RNA to be used in the present invention has an effect of inhibiting the expression of a gene encoding human plasma membrane-associated sialidase (NEU3).

The definition and measurement method of the effect are described above.

The double-stranded RNA to be used in the present invention further has an effect of inhibiting proliferation of cancer cells and inducing apoptosis of cancer cells. The degree of inhibition of cancer cell proliferation can be measured by, for example, measuring the number of cells, total DNA level, total protein level and etc., or by a known method such as MTT assay. The phrase "has an effect of inhibiting proliferation of cancer cells" as used herein means that, in the case where cells into which the double-stranded DNA of the present invention is introduced and cells into which the double-stranded DNA of the present invention is not introduced are cultured under the same conditions except for the introduction of the double-stranded DNA of the present invention, the degree of proliferation of cancer cell is lower, or the degree of reduction in cancer cells is higher, in the cells into which the double-stranded DNA of the present invention is introduced than that in the cells into which the double-stranded DNA of the present invention is not introduced.

The degree of apoptosis induction can be measured by a known method such as TUNEL method, DNA fragmentation assay, FACS analysis method, Annexin method, or caspase activity measurement method.

The phrase "has an effect of inducing apoptosis" means that, in the case where the degree of apoptosis is measured using cells into which the double-stranded RNA of the present invention is introduced and cells into which the double-stranded RNA of the present invention is not introduced under the same conditions except for the introduction of the double-stranded RNA of the present invention, the degree of apoptosis is higher in the cells into which the double-stranded RNA of the present invention is introduced than that in the cells into which the double-stranded RNA of the present invention is not introduced.

The double-stranded RNA to be used in the present invention can be used as an active ingredient of a pharmaceutical composition for treating cancer or diabetes. The pharmaceutical composition inhibits the expression of a gene encoding human plasma membrane-associated sialidase (NEU3).

Introduction of the double-stranded RNA in the pharmaceutical composition of the present invention into human cells efficiently inhibits the expression of a human plasma membrane-associated sialidase (NEU3) gene, which is strongly suggested to be involved in cancer or diabetes. Meanwhile, the double-stranded RNA in the pharmaceutical composition of the present invention inhibits the expression of the gene, resulting in inhibition of proliferation of cancer cells and induction of apoptosis. From these facts, it is considered that the pharmaceutical composition of the present invention is effective for a gene therapy of cancer or diabetes.

The phrase "cancer or diabetes" as used herein is not particularly limited as long as it causes increase in the expression of a human plasma membrane-associated sialidase (NEU3) gene, and includes colon cancer, prostate cancer, head and neck cancer, for example.

That is, one embodiment of the present invention is a use of a double-stranded RNA that inhibits the expression of a gene encoding human plasma membrane-associated sialidase (NEU3) in manufacturing a pharmaceutical composition for treating cancer or diabetes. Meanwhile, another embodiment of the present invention is a method of treating cancer or diabetes, which comprises administering the pharmaceutical composition of the present invention to a human.

In general, the pharmaceutical composition of the present invention can be administered orally or parenterally to a human in combination with a pharmaceutically acceptable pharmaceutical carrier. The dosage form of the pharmaceutical composition of the present invention is not particularly limited and can be appropriately selected depending on therapeutic purposes. Specific examples thereof include a tablet, a pill, a powder a liquid, a suspension, an emulsion, a granule, a capsule, a syrup, a suppository, an injection, an ointment, a patch, an ophthalmic solution, and a nasal drop. In order to prepare a formulation, there may be used an additive such as a vehicle, a binder, a disintegrator, a lubricant, a stabilizer, a flavoring, a diluent, a surfactant, or a solvent for injection, which are widely used in a general drug as a pharmaceutical carrier.

The amount of the double-stranded RNA in the pharmaceutical composition of the present invention is not particularly limited and may be appropriately selected. For example, the siRNA is contained in the composition preferably within the range of 50 µg/ml to 300 µg/ml.

The administration form of the pharmaceutical composition of the present invention is not particularly limited and is appropriately determined depending on the dosage form, disease site of a patient, sex and age of a patient, other conditions, and degree of the symptom of the disease and so on.

The dosage of a double-stranded RNA in the pharmaceutical composition of the present invention is appropriately selected depending on the usage, patient's age and sex, degree of the disease, other conditions, and so on. Meanwhile, the double-stranded RNA in the pharmaceutical composition of the present invention may be administered once or several times a day.

The pharmaceutical composition of the present invention is considered to be effective for a treatment of cancer or diabetes. The pharmaceutical composition of the present invention may be used together with a known preventive/therapeutic agent for cancer or diabetes or may be used separately before or after treatment with the preventive/therapeutic agent. If the composition is used as above, the preventive/therapeutic effect on cancer or diabetes can be enhanced. The pharmaceutical composition of the present invention may further contain the above-described preventive/therapeutic agent for cancer or diabetes as an active ingredient, or alternatively the above-described preventive/therapeutic agent for cancer or diabetes and the pharmaceutical composition of the present invention may be separately commercialized and combined when used.

EXAMPLES

Hereinafter, the present invention will be described in more detail by way of examples, but the present invention is not limited to the following examples.

Example 1

Based on the sequence of a human plasma membrane-associated sialidase gene (see GenBank/DDBJ accession No. AB008185), five sequences of 19 nucleotides were selected as candidates for a double-stranded RNA inhibiting the expression of the gene.

These sequences have GC contents of about 50% and is less affected by their secondary structures, and do not correspond to any sequences over 17 nucleotides of any genes other than the human plasma membrane-associated sialidase gene, as clarified by BLAST search to all human genes.

RNA sequences (antisense strands) having sequences identical to the above-described five sequences are represented by SEQ ID NOS: 1 to 5, and 8, respectively.

SEQ ID NO: 1 represents an RNA sequence identical to a DNA comprising nucleotides 218-236 of GenBank/DDBJ accession No. AB008185; SEQ ID NO: 2 represents an RNA sequence identical to a DNA comprising nucleotides 704-722 of GenBank/DDBJ accession No. AB008185; SEQ ID NO: 3 represents an RNA sequence identical to a DNA comprising nucleotides 949-967 of GenBank/DDBJ accession No. AB008185; SEQ ID NO: 4 represents an RNA sequence identical to a DNA comprising nucleotides 1009-1027 of GenBank/DDBJ accession No. AB008185; SEQ ID NO: 5 represents an RNA sequence identical to a DNA comprising nucleotides 1321-1339 of GenBank/DDBJ accession No. AB008185; and SEQ ID NO: 8 represents an RNA sequence identical to a DNA comprising nucleotides 833-857 of GenBank/DDBJ accession No. AB008185.

Example 2

A double-stranded RNA to be contained in the pharmaceutical composition of the present invention was produced.

That is, double-stranded RNAs each having the above-described five sequences (siRNAs) were prepared by using Silencer siRNA Construction kit (manufactured by Ambion, Inc.). The preparation was carried out in accordance with the method described in the instructions attached to the kit. Specifically, the preparation was carried out as follows.

First, two kinds of oligonucleotides including a sequence of a siRNA of interest and a leader sequence were synthesized for a sense strand and an antisense strand, respectively. Both these oligonucleotides were allowed to hybridize with T7 promoter primers (sequences identical to a T7 RNA promoter sequence and a leader sequence). A template DNA for siRNA transcription was synthesized using Exo-Klenow DNA polymerase. In vitro transcription reaction was carried out with T7 RNA polymerase to separately synthesize a sense strand RNA and an antisense strand RNA. Both strands were allowed to hybridize to prepare a double-stranded RNA. The unhybridized leader sequence of eight nucleotides was decomposed by a single-strand-specific RNase treatment. A DNase treatment was carried out to decompose the template DNA. Thereafter, the siRNAs were purified.

The siRNAs having a sequence represented by SEQ ID NOS: 1 to 5 were separately produced by biosynthesis based on such in vitro transcription reaction and used as test samples 1 to 5, respectively. The concentrations of the siRNAs in the test samples 1 to 5 were 75 µM, 63 µM, 61 µM, 65 µM, and 74 µM, respectively.

Meanwhile, the same five siRNAs were prepared by chemical synthesis (commissioned to Dharmacon Inc.).

Moreover, as a control, a scramble control sequence, modified by exchanging nucleotides in the nucleotide sequence represented by SEQ ID NO: 1 at random so that the sequence cannot recognize a target site, was produced by chemical synthesis and used as a test sample 6. Meanwhile, for the nucleotide sequences represented by SEQ ID NOS: 2 to 5, scramble control sequences were separately produced by chemical synthesis in the same way as above and used as test samples 7 to 10, respectively.

Example 3

For the respective test samples 1 to 10, samples for cell introduction were prepared. Specifically, the preparation was carried out by the following procedure.

For the respective test samples 1 to 10, solution A (a mix solution of 1.0 µl of Lipofectamine™ 2000 (manufactured by Invitrogen Corporation) and 2501 of Opti-MEM I (registered trademark, manufactured by GIBCO)) and solution B (a mix solution of 4 µg of a test sample and 250 µl of Opti-MEM I (manufactured by GIBCO Inc.)) were prepared. The solution A and solution B were separately allowed to stand at room temperature for 5 minutes and then mixed together, and the mixture was allowed to stand at room temperature for 20 minutes, thereby test samples 1 to 10 for cell introduction were prepared for the respective test samples 1 to 6.

Example 4

The test samples 1 to 10 for cell introduction were transiently introduced into human results were obtained. Also in a similar experiment using the colon cancer DLD-1 cells instead of the human uterine cervix cancer HeLa cells, almost the same results were obtained.

Example 6

Effects of the siRNAs on the expression of a plasma membrane-associated sialidase gene were examined by measuring the sialidase activity using the transfected cells which was prepared in Example 4.

The sialidase activity was measured as follows.

The human uterine cervix cancer HeLa cells transfected with the test samples 3 and 4 for cell introduction were cultured in DMEM medium for 48 hours. The cells were collected and washed with ice-cooled physiological saline, followed by sonication for 10 seconds, to thereby prepare crude cell extract solutions.

For the cell extract solutions thus obtained the sialidase activity was measured using ganglioside as a substrate. The reaction system containing 10 µl of 0.5 M sodium acetate (pH 4.6), 5 µl of 1% Triton X-100, 10 nmol ganglioside, and 10 µl of the cell crude extract solutions was adjusted to a total volume of 50 µl with distilled water. The 50 µl solutions was incubated at 37° C. for 30 to 60 minutes, and then 10 µl of the solutions was used to label free sialic acid with fluorescence using DMB (1,2-diamino-4,5-methylenedioxybenzen), followed by quantitative analysis by high performance liquid chromatography. The free sialic acid was analyzed in accordance with J. Chromatogr. 377, 111-119 (1986).

Meanwhile, for a crude cell extract solution obtained from untransfected cells, the sialidase activity was measured as a control.

The results revealed that the sialidase activity of the cells transfected with the test sample 3 for cell introduction, which was found to have little effect of inhibiting the expression of the mRNA of the plasma membrane-associated sialidase gene in Example 5, was a specific activity approximately equal to that of the control (5.6 units/mg protein). On the other hand, the sialidase specific activity of the cells transfected with the test sample 4 for cell introduction, which was found to inhibit the expression of the mRNA of the plasma membrane-associated sialidase by 94% in Example 5, was inhibited to 1.0 unit/mg·protein.

This showed that the siRNA having the sequence represented by SEQ ID NO: 4 had the effect of inhibiting the expression of the plasma membrane-associated sialidase gene at protein level as well as mRNA level. From this result, it was predicted that the siRNA having the sequence represented by SEQ ID NO: 2 had the effect of inhibiting the expression of the plasma membrane-associated sialidase gene at protein level as well as mRNA level.

In a similar experiment using the colon cancer DLD-1 cells instead of the human uterine cervix cancer HeLa cells, almost the same results were obtained.

Example 7

In order to examine the effect of inhibiting the expression of a plasma membrane-associated sialidase gene by the siRNAs to be used in the present invention on cell proliferation of cancer cells, MTT assay was carried out using Premix WST-1 Cell Proliferation Assay System (Takara Bio Inc.).

The MTT assay is based on the fact that MTT (one of tetrazolium salts) is decomposed into formazan dye by succinate-tetrazolium reductase which is present in mitochondria of living cells. The levels of living cells in samples can be compared by comparing absorbances of sample solutions stained with the formazan dye.

Cells transfected with the test samples 2, 3, 4, and 9 for cell introduction were separately cultured at $1 \times 10^4$ to $7 \times 10^4$ cells/well in a 96-well plate, and sampling was performed 12, 24, and 48 hours after the initiation of culture. To the respective samples was added 10 μl of a solution containing a tetrazolium salt and an electron-coupling reagent, and the samples were incubated for 30 minutes, followed by measurement of the absorbances at 450 nm of the formazan product using a microplate reader.

The results are shown in FIG. 1 below.

As shown in FIG. 1, the cells transfected with the test sample 2 for cell introduction and cells transfected with the test sample 4 for cell introduction were found to have more effects of inhibiting cell proliferation, as compared with the cells transfected with the test sample 9 (control) for cell introduction. In particular, the cells transfected with the test sample 4 for cell introduction was found to have the most excellent effect of inhibiting cell proliferation. Meanwhile, the cells transfected with the test sample 3 for cell introduction proliferated in the same degree as the control and was found to have little effect of inhibiting cell proliferation.

These results revealed that the siRNA having the sequence represented by SEQ ID uterine cervix cancer HeLa cells and colon cancer DLD-1 cells, respectively. Specifically, the introduction was carried out by the following method.

Human uterine cervix cancer HeLa cells and colon cancer DLD-1 cells were suspended in DMEM medium and cultured in a plate until the cell density became 70 to 80% confluent. The test samples 1 to 10 for cell introduction were separately added to the culture solutions of the above-described cells, to thereby transfect the cells.

Example 5

Effects of the above-described siRNAs on the expression of a plasma membrane-associated sialidase gene were examined by quantifying the mRNA levels of the gene using the transfected cells which was prepared in Example 4.

The total RNAs were extracted from the uterine cervix cancer HeLa cells (cultured for 48 hours after the transfection) transfected with the test samples 1 to 10 for cell introduction, and the cDNAs thereof were synthesized using a reverse transcriptase. Real-time PCR was carried out using the cDNAs, and the mRNA level of the plasma membrane-associated sialidase gene was quantified. The mRNA of interest was detected using primers prepared based on the sequence of the gene of interest. The sequences of the primers are shown in SEQ ID NOS: 6 and 7.

To correct the difference upon preparation between the samples, the miRNA level of a housekeeping gene, porphobilinogen deaminase (PBGD), was quantified in the same way as above.

The results of the tests revealed that the siRNAs from the test samples to 5 inhibited the expression of the plasma membrane-associated sialidase gene, as compared with the test samples 6 to 10 (scramble controls for the respective samples) as described below.

Test sample 4: the expression was inhibited by 94%

Test sample 2: the expression was inhibited by 45%

Test samples 1, 3, and 5: the expression was inhibited by 0 to 15%

As described above, the test samples 2 and 4 inhibited the expression, while the test samples 1, 3, and 5 did not significantly inhibit the expression.

Also in the case of using the siRNA produced by chemical synthesis instead of the siRNAs produced by biosynthesis based on in vitro transcription reactions, almost the same NO: 2 or 4 had more effects of inhibiting proliferation of the human uterine cervix cancer HeLa cells as compared with the control (the scramble control sequence for SEQ ID NO: 4). In particular, the siRNA having the sequence represented by SEQ ID NO: 4 was found to have an excellent effect of inhibiting cell proliferation. Meanwhile, the siRNA having the sequence represented by SEQ ID No: 3, which did not inhibit the expression of the plasma membrane-associated sialidase gene at mRNA and protein levels, was found to have no effect of inhibiting the proliferation of cancer cells.

In a similar experiment using the colon cancer DLD-1 cells instead of the human uterine cervix cancer HeLa cells, almost the same results were obtained.

Example 8

In order to examine the effect of inhibiting the expression of a human plasma membrane-associated sialidase gene by the siRNAs to be used in the present invention on apoptosis of cancer cells, the apoptosis level was measured by the TUNEL method using In Situ Cell Death Detection Kit, Fluorescein (manufactured by Roche Corp.). Specifically, the measurement was carried out by the following method in accordance with the instructions of the kit.

First, cells transfected with the test sample 4 for cell introduction ($1 \times 10^6$ cells) were fixed with paraformaldehyde at room temperature for 30 minutes. The sample was washed with distilled water and subjected to a membrane permeation treatment with a penetrating solution for two minutes with ice-cooling. Subsequently, the sample was washed again, and the TUNEL reaction mixture (containing TdT and dUTP) containing an enzyme and a label was added thereto, and the sample was incubated at 37° C. for 60 minutes.

Meanwhile, the same treatment as descried above was carried out using cells transfected with the test sample 3 for cell introduction instead of the cells transfected with the test sample 4 for cell introduction.

Thereafter, the number of dUTP fluorescent dye (FITC) linked to DNA fragments by TdT (terminal deoxynucleotidyl transferase) in both the samples was detected using a flow cytometer (manufactured by Becton Dickinson). In this process, fluorescence having wavelength of FL1 (530 nm±15 nm) was detected using an excitation light having a wavelength of 488 nm.

The results are shown in FIG. 2.

The results of FIG. 2 revealed that, in the case of the cells transfected with the test sample 4 for cell introduction, apoptosis was induced in 91.3% of the cells. That is, the double-stranded RNA of the present invention (the siRNA having the sequence represented by SEQ ID NO: 4) was found to induce apoptosis of cancer cells.

In a similar experiment using the colon cancer DLD-1 cells instead of the human uterine cervix cancer HeLa cells, almost the same results were obtained.

Example 9

The siRNA having the sequence represented by SEQ ID NO: 8 was synthesized (commissioned to iGENE Therapeutics, Inc.).

In the same way as Examples 3 and 4, the above-described siRNA was transiently introduced into the HeLa cells. Then, in the same way as Example 5, the mRNA level of NEU3 was quantified. In addition, in the same way as Example 8, the degree of apoptosis was measured by the TUNEL method. A double-stranded RNA having the nucleotide sequence represented by SEQ ID NO: 9 was used as a scramble control.

The results revealed that the expression of the mRNA of NEU3 was inhibited by 94%. Meanwhile, apoptosis was induced in 85% of the cells.

INDUSTRIAL APPLICABILITY

The double-stranded RNA in the pharmaceutical composition of the present invention efficiently inhibits the expression of a human plasma membrane-associated sialidase (NEU3) gene, which is strongly suggested to be involved in cancer or diabetes. Meanwhile, the double-stranded RNA in the pharmaceutical composition of the present invention inhibits the expression of the gene, resulting in inhibition of proliferation of cancer cells and induction of apoptosis. The results revealed that the pharmaceutical composition of the present invention is effective for a gene therapy of cancer or diabetes.

BRIEF DESCRIPTION OF THE DRAWINGS

FIG. 1 is a graph showing the effects of inhibiting cancer cell proliferation by introduction of the siRNAs.

FIG. 2 is a graph showing the effects of the siRNAs on cell death.

What is claimed is:

1. A composition comprising a double-stranded RNA shown in (A) or (B):
   (A) a double-stranded RNA wherein one strand is the sequence represented by SEQ ID NO: 2;
   (B) a double-stranded RNA which is 20 to 30 nucleotides in length and contains the sequence of SEQ ID NO: 2;
   wherein the double-stranded RNA inhibits the expression of a gene encoding human plasma membrane-associated sialidase (NEU3).

2. The composition according to claim 1, wherein the double-stranded RNA is 20 to 27 nucleotides in length.

3. The composition according to claim 1, wherein the double-stranded RNA further comprises 3'-protruding end of 1 to 4 nucleotides.

4. A composition comprising a vector having a nucleotide sequence capable of expressing the double-stranded RNA of claim 1 in human cells.

5. The composition according to claim 1, wherein the composition is for treating cancer cells that have increased expression of the human plasma membrane-associated sialidase (NEU3) gene compared to non-cancer cells.

6. A method for treating cancer cells that have increased expression of the human plasma membrane-associated sialidase (NEU3) gene compared to non-cancer cells, wherein the method comprises administering the composition of claim 1 to a human subject in need thereof.

7. The method of claim 6, wherein the composition comprises double-stranded RNA which is 20 to 27 nucleotides in length.

8. The method of claim 6, wherein the composition comprises double-stranded RNA having a 3'-protruding end of 1 to 4 nucleotides.

9. The method of claim 6, wherein the composition comprises a vector having a nucleotide sequence capable of expressing the double-stranded RNA in human cells.

* * * * *

UNITED STATES PATENT AND TRADEMARK OFFICE
CERTIFICATE OF CORRECTION

PATENT NO. : 7,795,233 B2
APPLICATION NO. : 11/719517
DATED : September 14, 2010
INVENTOR(S) : Miyagi et al.

It is certified that error appears in the above-identified patent and that said Letters Patent is hereby corrected as shown below:

Column 6, Line 9, "using primers design" should be changed to --using primers designed--

Column 8, Line 6, "a powder a liquid," should be changed to --a powder, a liquid,--

Column 9, Line 63, "introduction were," should be changed to --introduction were--

Column 9, Line 66, "solution of 1.0 µl" should be changed to --solution of 10 µl--

Column 9, Line 67, "and 2501 of" should be changed to --and 250 µl of--

Column 10, Line 13, after "into human" should be inserted the following:

--uterine cervix cancer HeLa cells and colon cancer DLD-1 cells, respectively. Specifically, the introduction was carried out by the following method.

Human uterine cervix cancer HeLa cells and colon cancer DLD-1 cells were suspended in DMEM medium and cultured in a plate until the cell density became 70 to 80% confluent. The test samples 1 to 10 for cell introduction were separately added to the culture solutions of the above-described cells, to thereby transfect the cells.

Example 5

Effects of the above-described siRNAs on the expression of a plasma membrane-associated sialidase gene were examined by quantifying the mRNA levels of the gene using the transfected cells which was prepared in Example 4.

The total RNAs were extracted from the uterine cervix cancer HeLa cells (cultured for 48 hours after the transfection) transfected with the test samples 1 to 10 for cell introduction, and the cDNAs thereof were synthesized using a reverse transcriptase. Real-time PCR was carried out using the cDNAs, and the mRNA level of the plasma membrane-associated sialidase gene was quantified. The mRNA of interest was detected using primers prepared based on the sequence of the gene of interest. The sequences of the primers are shown in SEQ ID NOS: 6 and 7.

Signed and Sealed this
Tenth Day of May, 2011

David J. Kappos
*Director of the United States Patent and Trademark Office*

CERTIFICATE OF CORRECTION (continued)

To correct the difference upon preparation between the samples, the mRNA level of a housekeeping gene, porphobilinogen deaminase (PBGD), was quantified in the same way as above.

The results of the tests revealed that the siRNAs from the test samples 1 to 5 inhibited the expression of the plasma membrane-associated sialidase gene, as compared with the test samples 6 to 10 (scramble controls for the respective samples) as described below.

Test sample 4: the expression was inhibited by 94%

Test sample 2: the expression was inhibited by 45%

Test samples 1, 3, and 5: the expression was inhibited by 0 to 15%

As described above, the test samples 2 and 4 inhibited the expression, while the test samples 1, 3, and 5 did not significantly inhibit the expression.

Also in the case of using the siRNA produced by chemical synthesis instead of the siRNAs produced by biosynthesis based on *in vitro* transcription reactions, almost the same--

Column 10, Line 31, "thus obtained the" should be changed to --thus obtained, the--

Column 10, Line 51, "(5.6 units mg protein)." should be changed to --(5.6 units mg·protein).--

Column 11, Lines 36-67 and Column 12, Lines 1-16, after SEQ ID, the section beginning "uterine cervix cancer" and ending "almost the same" should be deleted.

```
                        SEQUENCE LISTING

<160> NUMBER OF SEQ ID NOS: 9

<210> SEQ ID NO 1
<211> LENGTH: 19
<212> TYPE: RNA
<213> ORGANISM: Artificial Sequence
<220> FEATURE:
<223> OTHER INFORMATION: synthetic RNA

<400> SEQUENCE: 1
ggaagaugac agagggauu                                                  19

<210> SEQ ID NO 2
<211> LENGTH: 19
<212> TYPE: RNA
<213> ORGANISM: Artificial Sequence
<220> FEATURE:
<223> OTHER INFORMATION: synthetic RNA

<400> SEQUENCE: 2
guauaccuac uacaucccu                                                  19

<210> SEQ ID NO 3
<211> LENGTH: 19
<212> TYPE: RNA
<213> ORGANISM: Artificial Sequence
<220> FEATURE:
<223> OTHER INFORMATION: synthetic RNA

<400> SEQUENCE: 3
gugaaggcuu ucagagacu                                                  19

<210> SEQ ID NO 4
<211> LENGTH: 19
<212> TYPE: RNA
<213> ORGANISM: Artificial Sequence
<220> FEATURE:
<223> OTHER INFORMATION: synthetic RNA

<400> SEQUENCE: 4
```

-continued aagggagugu gguaaguuu                                            19

<210> SEQ ID NO 5
<211> LENGTH: 19
<212> TYPE: RNA
<213> ORGANISM: Artificial Sequence
<220> FEATURE:
<223> OTHER INFORMATION: synthetic RNA

<400> SEQUENCE: 5
guuuguuuga auguggqac                                            19

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gactggtcat ccctgcgtat                                           20

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
gagccatgat tctgacggtgt t                                        22

<210> SEQ ID NO 8
<211> LENGTH: 25
<212> TYPE: RNA
<213> ORGANISM: Artificial Sequence
<220> FEATURE:
<223> OTHER INFORMATION: synthetic RNA

<400> SEQUENCE: 8
gguuacagua gaaugugaag uggca                                     25

<210> SEQ ID NO 9
<211> LENGTH: 19
<212> TYPE: RNA
<213> ORGANISM: Artificial Sequence
<220> FEATURE:
<223> OTHER INFORMATION: synthetic RNA

<400> SEQUENCE: 9
gcgauuaaug uagguucga                                            19